United States Patent [19]

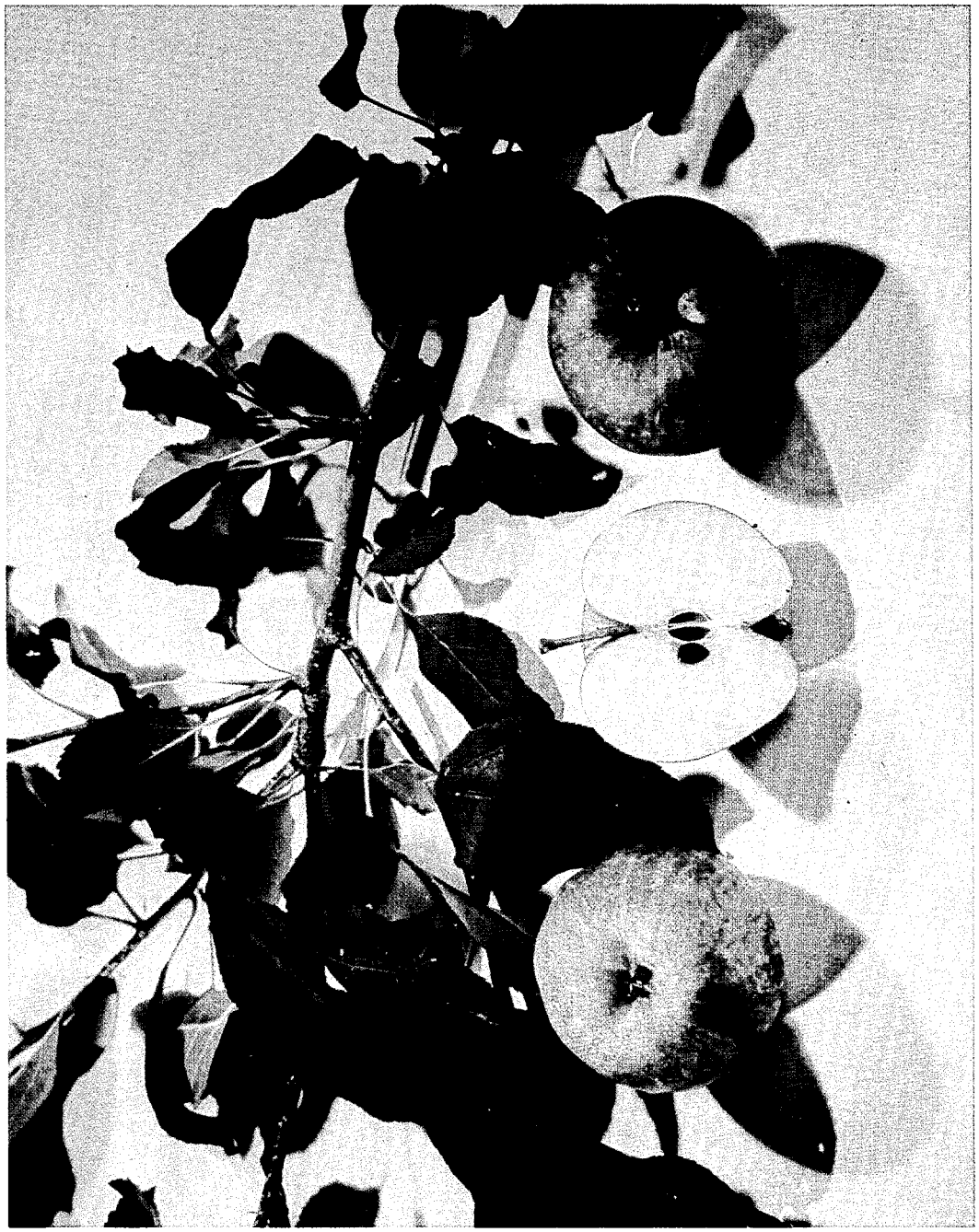

Ten Hove

[11] Plant 4,121

[45] Oct. 4, 1977

[54] APPLE TREE—ROYAL GALA VARIETY

[75] Inventor: Hendrik Willem Ten Hove, Matamata, New Zealand

[73] Assignee: Stark Brothers Nurseries & Orchards Company, Louisiana, Mo.

[21] Appl. No.: 709,506

[22] Filed: July 28, 1976

[51] Int. Cl.[2] ..... A01H 5/03

[52] U.S. Cl. ..... Plt./34

[58] Field of Search ..... Plt./34

*Primary Examiner*—Robert E. Bagwill

*Attorney, Agent, or Firm*—Burns, Doane, Swecker & Mathis

[57] ABSTRACT

The new and distinct variety of apple tree is a mutation of the Gala apple tree (U.S. Plant Pat. No. 3,637). The fruit of the apple tree of the new variety exhibits an attractive appearance and unlike the parent variety possesses an all over bright red color overlaid with obscure darker broad striping. The new variety has been named the Royal Gala variety.

1 Drawing Figure

SUMMARY OF THE INVENTION

The new variety which is a mutation of the Gala variety (U.S. Plant Pat. No. 3,637) was found by me during March, 1969 as a single bud sport or limb mutation among the trees growing at Matamata, New Zealand. I was attracted to the new variety because of the attractive and distinctive color of its fruit. Asexual reproduction of my discovery was first performed during March, 1970. The new variety has been named the Royal Gala variety. Asexual propagation shows that the unique combination of characteristics and distinctive color come true to form and are established and transmitted through succeeding propagations.

BRIEF DESCRIPTION OF THE DRAWING

The accompanying drawing shows typical specimens of the foliage and fruit of the new variety as depicted in color as nearly true as is reasonably possible to make the same in a color illustration of this character.

DETAILED DESCRIPTION OF THE DISCLOSURE

The following is a detailed description of my new variety with color terminology in accordance with Ridgway's Color Standards and Nomenclature except where general color terms of ordinary dictionary significance are obvious.

The specimens described were grown at Matamata, New Zealand.

The first and last pickings were Feb. 25, 1976 and Apr. 1, 1976 in New Zealand.

Tree: Small; vigorous; spreading; low; round-topped; slow growing; hardy; productive; regular bearing.

Trunk: Medium; smooth.

**Branches: Medium thick; smooth; much branching; Light Mouse Gray Plate LI, Color No. 15''''', tone *b* of Ridgway Color Standards.**

*Lenticels.*—Numerous; medium large.

Leaves: Length, 3½ inches; Width, 1¾ inches; medium large; medium wide; medium long; oval; abruptly pointed; Empire Green Plate XXXII, Color No. 33'', **tone *b* of Ridgway Color Standards; smooth.**

*Margin.*—Crenate.

Flowers: Dates of first and full bloom (in New Zealand), Oct. 18, 1975 - Oct. 30, 1975; medium early; Size, medium small; Color, white with pink on reverse side.

Fruit: Maturity when described, eating ripe.

*Size.*—Uniform; axial diameter, 2½ inches; transverse, 2¾ inches; form, globose.

*Cavity.*—Symmetrical; abrupt at base; apex acuminate; depth, ⅞ inch; breadth, ½ inch; markings, none.

*Basin.*—Symmetrical; rounded; wide; undulate; depth, 5/16 inch; breadth, ¾ inch; markings, none.

Stem: Medium stout; length, about ⅞ inch; breadth, about 3/32 inch.

Calyx: Closed.

*Segments.*—Broadly lanceolate; approximate; reflexed from base at apex.

*Outer surface.*—Pubescent.

*Inner Surface.*—Pubescent.

Eye: Medium.

Skin: Thin; smooth; glossy; waxed. Dots obscure; many; even; small; circular.

*Color of dots.*—Pale yellow.

*Ground color*—Plate XVI, Color No. 21', tone *b* of Ridgway Color Standards.

*Color markings.*—Striped; self-colored; very bright.

*Color of markings.*—Rose Doree Plate I, Color No. 3, tone *b* of Ridgway Color Standards.

*Bloom.*—Wanting; white with pink on reverse.

*General color effect.*—Glossy bright red; self-colored; overlaid with obscure darker broad striping in some fruit; very attractive appearance.

Flesh: Juicy; satiny; creamy white.

*Texture.*—Firm; tender; fine; crisp.

*Flavor.*—Mild; delicate; rich.

*Quality.*—Best.

Core: Sessile; medium.

*Bundle area (longitudinal section).*—Small; oblate.

*Bundles.*—Inconspicuous; in one whorl.

*Core lines.*—Clasping; indistinct.

*Calyx-tube.*—Glabrous toward base; funnel form.

*Stem of funnel.*—Long.

*Depth of tube to shoulder.*—3/16 inch.

*Entire depth.*—½ inch.

*Styles.*—Present.

*Stamens.*—In one distinct whorl; median.

*Auxiliary cavity.*—Present.
*Seed cells.*—Axile; open.
*Cell walls.*—Thin.
*Length.*—9/16 inch.
*Breadth.*—$\frac{1}{8}$ inch.
*Longitudinal section.*—Orbicular; obtuse at apex.
*Surface.*—Smooth.
*Cross section.*—Broad.
Seeds: Number perfect: 10.
*Number in one cell.*—2.
*Length.*—5/16 inch.
*Breadth.*—3/16 inch.
*Color.*—Burnt Umber Plate XXVIII, Color No. 9″, tone *m* of Ridgway Color Standards.

Use: Market; dessert.
Keeping quality: Good.
Resistance to:
*Insects.*—Good.
*Diseases.*—Good.

I claim:

1. A new and distinct variety of apple tree which is a mutation of the Gala variety (U.S. Plant Pat. No. 3,637) substantially as shown and described, characterized by an all over bright red color overlaid with obscure darker broad striping.

* * * * *

UNITED STATES PATENT AND TRADEMARK OFFICE

CERTIFICATE OF CORRECTION

PATENT NO. : Plant Patent No. 4,121

DATED : October 4, 1977

INVENTOR(S) : Hendrik Willem Ten Hove

It is certified that error appears in the above-identified patent and that said Letters Patent is hereby corrected as shown below:

Delete the present Title and insert -- APPLE TREE - TENROY VARIETY --.

In the Abstract at line 2, delete "Gala" and insert -- Kidd's D-8 --.

In Col. 1 at line 2, delete "Gala" and insert -- Kidd's D-8 --.

In Col. 1 at line 10, delete "Royal Gala" and insert -- Tenroy --.

In Claim 1 at line 2, delete "Gala" and insert -- Kidd's D-8 --.

Signed and Sealed this

*Twenty-third* Day of *April 1985*

[SEAL]

*Attest:*

DONALD J. QUIGG

*Attesting Officer* *Acting Commissioner of Patents and Trademarks*

UNITED STATES PATENT AND TRADEMARK OFFICE

CERTIFICATE OF CORRECTION

PATENT NO. : Plant Patent No. 4,121

DATED : October 4, 1977

INVENTOR(S) : Hendrik Willem Ten Hove

It is certified that error appears in the above-identified patent and that said Letters Patent is hereby corrected as shown below:

In the Abstract at the last line, delete "Royal Gala" and insert -- Tenroy --.

Signed and Sealed this

*Seventh* Day of *January 1986*

[SEAL]

*Attest:*

DONALD J. QUIGG

*Attesting Officer*

*Commissioner of Patents and Trademarks*